United States Patent
Suissa

(10) Patent No.: US 9,248,212 B2
(45) Date of Patent: Feb. 2, 2016

(54) FRAGRANCE CAPSULE AND ASSOCIATED FRAGRANCE-DIFFUSING DEVICE

(75) Inventor: David Suissa, Vincennes (FR)

(73) Assignee: PRESENSIA (FR)

( * ) Notice: Subject to any disclaimer, the term of this patent is extended or adjusted under 35 U.S.C. 154(b) by 65 days.

(21) Appl. No.: 14/237,086

(22) PCT Filed: Jul. 26, 2012

(86) PCT No.: PCT/FR2012/051781
§ 371 (c)(1),
(2), (4) Date: Feb. 26, 2014

(87) PCT Pub. No.: WO2013/021114
PCT Pub. Date: Feb. 14, 2013

(65) Prior Publication Data
US 2014/0178213 A1    Jun. 26, 2014

(30) Foreign Application Priority Data

Aug. 5, 2011   (FR) ...................... 11 57183

(51) Int. Cl.
| A61L 9/00 | (2006.01) |
| B01D 39/00 | (2006.01) |
| A61L 9/12 | (2006.01) |
| A61L 9/04 | (2006.01) |

(52) U.S. Cl.
CPC ................. *A61L 9/122* (2013.01); *A61L 9/042* (2013.01); *A61L 9/12* (2013.01); *A61L 2209/15* (2013.01)

(58) Field of Classification Search
CPC ............ A61L 9/00; A61L 9/032; A61L 9/04; A61L 9/12
USPC .................. 422/5, 120, 123, 306; 96/222
See application file for complete search history.

(56) References Cited

U.S. PATENT DOCUMENTS 4,968,456 A * 11/1990 Muderlak et al. ............. 422/122
2008/0061453 A1 3/2008 Diaz

FOREIGN PATENT DOCUMENTS

| EP | 0104758 | 4/1984 |
| FR | 1500142 | 11/1967 |
| JP | 2002291392 A | 10/2002 |
| WO | 9940950 | 8/1999 |
| WO | 03105652 A2 | 12/2003 |
| WO | 2004096588 | 11/2004 |
| WO | 2006029690 A1 | 3/2006 |
| WO | 2006046940 | 5/2006 |
| WO | 2008044201 A2 | 4/2008 |
| WO | 2009003704 | 1/2009 |

OTHER PUBLICATIONS

International Search Report for corresponding application PCT/FR2012/051781 filed Jul. 26, 2012; mail date Nov. 20, 2012.

* cited by examiner

*Primary Examiner* — Monzer R Chorbaji
(74) *Attorney, Agent, or Firm* — Cantor Colburn LLP

(57) ABSTRACT

A fragrance capsule and a diffusing device therefor, the capsule including
   substrate elements into which a fragrance is adsorbed,
   a frame,
   a first grille and a second grille which are fixed in the frame facing one another, each grille having a plurality of bars, where
the bars of one and the same grille being spaced apart and the grilles being spaced apart, so that the capsule allows a single layer of substrate elements to be held in the frame and between the grilles and allows air to circulate through the frame around the substrate elements and the bars.

12 Claims, 3 Drawing Sheets

US 9,248,212 B2

FRAGRANCE CAPSULE AND ASSOCIATED FRAGRANCE-DIFFUSING DEVICE

TECHNICAL FIELD

The invention relates in general to the field of the diffusion of fragrance and supports for scented substances.

BACKGROUND

Supports for scented substances can be classified as follows:

reservoirs of scented substances in the liquid state which are intended to be vaporized either by micronization using the Venturi effect which may or may not be coupled with microvibrations, or using a wick employing the effect of capillarity when subjected to an air flow;

materials which pass from the solid state to the liquid state and then to the vapor state under the effect of heat, the classical example being a scented candle;

wet supports soaked with substances, such as scented wipes; and solid supports into which scented molecules are adsorbed and released into the atmosphere by spontaneous diffusion or diffusion assisted by air flow, for example certain scented filters used in automotive cabin interiors or dry capsules of polymers used in certain devices that diffuse ambient fragrances.

The invention relates to this last category of supports and more particularly to a fragrance capsule comprising substrate elements into which a fragrance is adsorbed. The invention also relates to an associated fragrance-diffusing device.

As far as the prior art is concerned, dry capsules of polymer beads are described for example in document EP1054697. In that document, a capsule is placed in a cylindrical duct made in a plug of spherical overall shape so that the capsule can be isolated from the environment by turning the plug when scent is not to be diffused. However, that document provides no specific detail regarding how the beads are positioned inside the capsule.

Furthermore, document EP0104758 describes a capsule provided with a protective member for hermetically isolating it from the ambient air when not in use. That document provides no specific detail regarding how the beads are positioned in the capsule.

The same is true of documents FR1500142, WO03105652, WO2009003704 and WO2006046940 which provide no information regarding any special positioning of the scented elements.

BRIEF SUMMARY

That being so, the present invention proposes a fragrance capsule which has at least one technical advantage over the supports mentioned hereinabove.

To that end, the fragrance capsule comprises:
substrate elements into which a fragrance is adsorbed,
a frame,
a first grille and a second grille which are fixed in the frame facing one another, each grille comprising a plurality of bars, the bars of one and the same grille being spaced apart and the grilles being spaced apart, so that the capsule allows a single layer of substrate elements to be held in the frame and between the grilles and allows air to circulate through the frame around the substrate elements and the bars.

The fact that the substrate elements are arranged in the capsule in a single layer offers several advantages. First, the total surface area of substrate elements in contact with the air circulating through the frame is optimized, or even maximized, for a given number of substrate elements. Secondly, the rate at which the fragrance is desorbed into the atmosphere is practically the same for each substrate element. Thirdly, the thickness of the capsule, or, which is the equivalent, the thickness of the frame, is relatively small in comparison with its other dimensions, making the capsule compatible with compact fragrance-diffusing devices. Fourthly, an air flow passing through the capsule is uniformly distributed across the substrate elements and perfect fragrance quality is thus obtained.

Furthermore, because the capsule is intended to be inserted in a compact fragrance-diffusing device comprising at least one air flow generator suitable for making air circulate from upstream of the capsule to downstream, the following advantages are also achieved. First, satisfactory diffusion by the device of the fragrance molecules into the atmosphere requires a lower pressure than would be required if the substrate elements were arranged in at least two layers, thus reducing to a corresponding extent the requirements that the air flow generator has to meet. Secondly, the rate of flow of fragrance molecules diffused is practically unchanging, and so the quantity of fragrance molecules diffused in a given period of time and as a function of the volume of the room that is to be scented can be metered easily and accurately.

According to one specific feature, each substrate element has dimensions which vary over time from initial dimensions to smaller final dimensions reached when the fragrance has been fully desorbed.

According to another particular feature, the first and second grilles are planar and mutually parallel, and the bars of each grille are straight and mutually parallel, so that each bar of the first grille faces a bar of the second grille.

The capsule is thus advantageously easy to manufacture on an industrial scale. Furthermore, the air flow passing through it is advantageously close to a laminar air flow downstream of the capsule.

According to another specific feature, for each grille, the distance between two adjacent first bars and the thickness of each bar are strictly smaller than the smallest dimension of the substrate elements, and the spacing between the first and second grilles is greater than the smallest initial dimension of the substrate elements and smaller than the largest initial dimension of the substrate elements.

Advantageously, the substrate elements are thus at least initially kept tightly packed, or at least wedged, between the bars of the grilles. Furthermore, as their dimensions shrink, the substrate elements become at least partially free to move around between the grilles, without in any way being able to pass between the bars.

According to another particular feature, at least two adjacent second bars of the first grille and/or the second grille extend in the thickness of the frame so that a single row of substrate elements of the layer of substrate elements is held between the two adjacent second bars extending in the thickness of the frame.

Advantageously, the layer of substrate elements thus comprises at least one row of substrate elements having a number of substrate elements that is relatively easy to control when filling the capsule with substrate elements on an industrial scale.

According to another particular feature, the adjacent second bars extending in the thickness of the frame are arranged vertically so that as the substrate elements of the row compact down over time at least under the action of their weight, the height of the row constitutes a visual indication of how used up the capsule is.

Thus, it is easy and simple to see how used up the capsule is.

According to a first alternative form, a weight is arranged on top of the row of beads. This then ensures that the row compacts down over time.

According to a second alternative form, the capsule 0 comprises a spring attached by a first end to the frame 2 in the region of the row and an end stop attached to the other end of the spring, so that the spring is kept compressed between the frame 2 and the end stop irrespective of how used up the substrate elements 1 are. This then ensures that the row compacts down over time whether it is arranged vertically or horizontally.

According to another particular feature, the frame comprises at least one male attachment element on one face and at least as many female attachment elements on the other face, each male element being able to engage with any one of the female elements so that several capsules can be joined together with their frames juxtaposed in the direction of their thickness.

Thus, the quantity of fragrance molecules diffused can be altered, notably according to the volume of the room that is to be scented.

According to another particular feature, an airtight seal is fitted at the junction between two juxtaposed frames.

The air flow passing through the capsules which are juxtaposed via their frames is thus forced to pass through each capsule of the juxtaposition without any loss of air flow pressure caused by air leaking between the frames of the juxtaposed capsules.

The invention also relates to a fragrance-diffusing device comprising:
- a capsule as itemized hereinabove,
- a ventilation passage,
- an air flow generator designed to propel air along the ventilation passage, and
- an attachment support designed for attaching the fragrance capsule in the ventilation passage,
- so that the propelled air diffuses the fragrance.

BRIEF DESCRIPTION OF THE DRAWINGS

Other features and advantages of the invention will become clearly apparent from the description thereof given hereinafter by way of entirely nonlimiting indication with reference to the attached drawings, in which.

DETAILED DESCRIPTION

Figure 5:
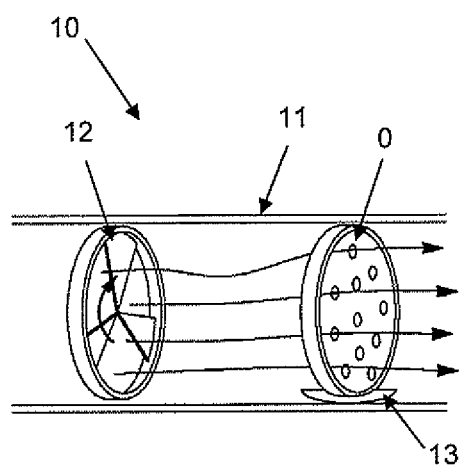

As illustrated in FIG. 5, the capsule 0 according to the invention is intended to be attached removably inside a fragrance-diffusing device 10 comprising:
- a ventilation passage 11,
- an air flow generator 12 designed to propel air along the ventilation passage, and
- an attachment support 13 designed to attach the fragrance capsule 0 inside the ventilation passage.

These elements of the device are arranged in such a way that the propelled air diffuses the fragrance. The air flow generator is more particularly a turbine and the air flow is preferably slightly pressurized in relation to atmospheric pressure. Typically, the overpressure of the air passing through the capsule is of the order of 0.10 to 0.80 inches H2O at 21° C., i.e. of the order of 25 to 200 pascals.

The capsule is disposable and replaced when it is used up. For that reason, it is envisaged that the fragrance-diffusing device will comprise means for inserting and removing at least one capsule into and from the ventilation passage 11 in the region of the attachment support 13. These insertion and removal means are arranged with or not with the attachment support 13. Moreover, the attachment support may just as easily allow the attachment of one capsule or of several mutually juxtaposed capsules, as described later on.

Figure 1:
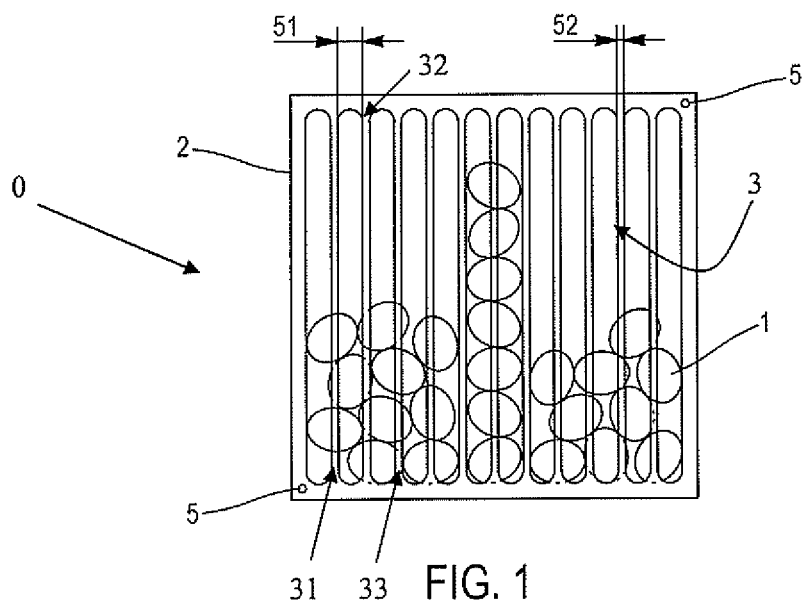
FIG. 1 depicts a front view of the capsule according to one embodiment.
Figure 2:
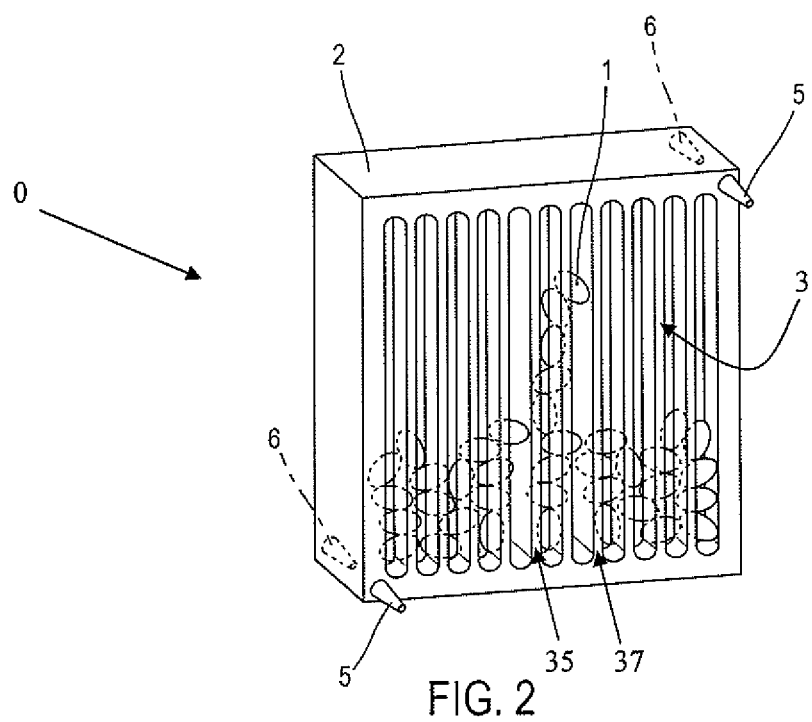
FIG. 2 depicts a perspective view of the capsule depicted in FIG. 1.
Figure 3:
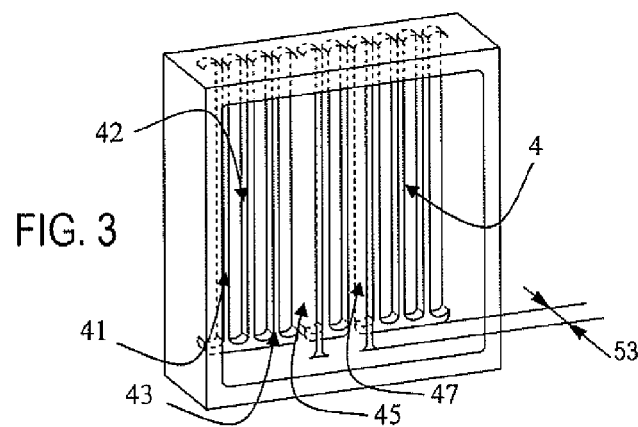
FIG. 3 depicts a perspective view of the capsule open, i.e. without the second grille.

In its broadest sense, and as depicted in FIGS. 1 to 3, the fragrance capsule 0 comprises:
- substrate elements 1 into which a fragrance is adsorbed,
- a frame 2,
- a first grille 3 and a second grille 4 which are fixed into the frame 2 facing one another, each of the grilles 3, 4 comprising a plurality of bars 31, 32, 33, . . . , 41, 42, 43, . . . .

The substrate elements are more particularly suited to allowing fragrance molecules to penetrate or fix at least at their periphery. As such, the substrate elements spontaneously diffuse small quantities of the fragrance modules they contain as a result of natural evaporation, or more particularly, through a desorption phenomenon.

The substrate elements are solid. They are made at least in part from a porous material and/or a polymer material.

Porous materials are composed of, for example, of ceramic or wood.

The substrate elements may adopt the shape of spheroids, rhombohedric or rectangular parallelepipeds, or prismatoids.

In a preferred embodiment, the substrate elements are spheroid beads made of polymer and the fragrance molecules are adsorbed into the entire volume of each bead. Depending on the polymer used and on the fragrance, the beads naturally diffuse the fragrance molecules for 6 to 18 months in a barely perceptible manner. One example of such a material is Pebax®.

By way of example, the polymer beads each have, before the fragrance is adsorbed, a smallest dimension of 3 mm and a largest dimension of 4 mm and, after the fragrance has been adsorbed, a smallest dimension of 4 mm and a largest dimension of 6 mm. The weight of fragrance adsorbed into each bead corresponds more or less to the weight of a bead before the fragrance is adsorbed.

The frame, the grilles and their bars are made of a material chemically able to withstand the fragrance. For example, this material is a plastic, such as a polyamide (PA). Plastics have the advantage of generally being inexpensive.

The frame, the grilles and their bars may also be made of a material which is inert to the fragrances. What is meant by a material that is inert to the fragrances is a material with which the fragrance molecules do not interact. Such a material can therefore not be impregnated or contaminated with the fragrances. Said material that is inert to the fragrances may, nonlimitingly, be aluminum, a metal such as copper or zinc, glass, or a material that has been surface-treated to make it inert to the fragrances. However, it should be noted that the capsule becoming contaminated with the scent of the fragrance does not really present any problems given that the capsule is disposable in its entirety and replaced after it is used up.

One of the two grilles, for example the grille 3, may be attached securely to the frame 2, or even form one piece with the frame 2, as has been illustrated in FIG. 3, so that this grille 3 forms with the frame 2 a receptacle that is open via that face of the frame 2 that is intended to accept the other grille 4, this other grille 4 being, for example, attached, either removably or non-removably, to the frame 2 after the receptacle has been filled with substrate elements 1.

The air flow passing through the capsule 0 causes an increase in the quantity of fragrance molecules diffused per unit time, as compared with the quantity of fragrance molecules that would be evaporated per unit time in the absence of an air flow. The desorption phenomenon effectively combines with the convection of the air flow. More particularly, the fragrance molecules at the periphery of the substrate elements are sort of plucked from the substrate by the air flow and as a result the fragrance molecules more deeply adsorbed into the substrate element are drawn toward the periphery of the element from which they in turn are plucked, etc.

According to one essential feature of the capsule 0 and as illustrated in FIGS. 1 and 2, the bars 31, 32, 33, . . . , 41, 42, 43, . . . of one and the same grille are spaced apart and the grilles 3, 4 are spaced apart, so that the capsule 0 is able to hold a single layer of substrate elements 1 in the frame 2 and between the grilles 3, 4. Circulation of air through the frame 2 around the substrate elements 1 and the bars 31, 32, 33, . . . , 41, 42, 43, . . . allows the fragrance to be diffused.

The substrate elements are thus arranged in the capsule in a single layer, and this offers several advantages.

Firstly, the total surface area of substrate elements in contact with the air circulating through the frame is optimized, or even maximized, for a given number of substrate elements. This is because fewer points of contact or smaller areas of contact between the substrate elements mean that the area of substrate elements swept by the air flow passing through the capsule is greater.

Secondly, the rate at which the fragrance is desorbed into the atmosphere is practically the same for each substrate element. In other words, each substrate element of the layer is exposed to the air flow in exactly the same way as the others.

Thirdly, the thickness of the capsule 0 or, which is equivalent, of the frame 2, is relatively small by comparison with its other dimensions, making the capsule compatible with compact fragrance-diffusing devices 10. Typically, the capsule has a width and a length/height of the order of a few centimeters and preferably equal to 5 cm, and a thickness of the order of 1 centimeter, and preferably equal to 0.8 cm. By way of example, the ventilation passage 11 of the fragrance-diffusing device has a cross section of a width and of a length/height that are appreciably higher than those of the capsule so that the capsule can be inserted with practically no clearance into the ventilation passage. Typically, the fragrance-diffusing device 10 takes the form of a parallelepiped 6 cm wide, 3 cm deep and 6 cm tall.

Fourthly, an air flow passing through the capsule is evenly distributed over the substrate elements and thus perfect fragrance quality is obtained. Specifically, the air flow thus entrains, from each substrate element of the layer, a quantity of fragrance molecules that is practically constant over a given period of time and practically identical between the various substrate elements. This quantity is more particularly tailored, at the time of manufacture of the substrate elements and accordingly to the fragrance that is to be diffused, to create a background scent that takes the quality of the fragrance into consideration.

Furthermore, as the air flow generator 12 of the fragrance-diffusing device is able to make air circulate from upstream to downstream of the ventilation passage 11, through the capsule 0, the following advantages are also obtained.

First, satisfactory diffusion of the fragrance molecules into the atmosphere by the air flow requires a lower pressure than would be required if the substrate elements were arranged in several layers. This is because for a constant air flow upstream of the capsule, the force of the air flow leaving the ventilation passage, i.e. downstream of the capsule, is greater if the fragrance elements are arranged in a single layer than if they were arranged in several layers. The requirements that the air flow generator has to meet are therefore correspondingly less demanding. Typically, the use of low power fans or turbines, which are therefore inexpensive and relatively quiet, is advantageously sufficient and satisfactory.

Secondly, the flow rate of fragrance molecules diffused is substantially unchanging and so the quantity of fragrance molecules diffused in a given period of time and according to the volume of the room that is to be scented can be metered easily and precisely.

Particularly when it is made of a polymer material, each substrate element 1 has dimensions which vary over time from initial dimensions to smaller final dimensions reached when the fragrance has been fully desorbed.

The initial dimensions of the substrate elements 1 are generally comprised between 1 mm and 15 mm. More particularly, the smallest initial dimension of the polymer beads is 4 mm and the largest initial dimension of the polymer beads is 6 mm, these corresponding precisely to the dimensions indicated earlier for polymer beads after the fragrance has been adsorbed.

The final dimensions of the polymer substrate elements 1 are comprised between one half and eight-tenths of their initial dimensions. More specifically, the smallest final dimension of the polymer beads is 3 mm and the largest final dimension of the polymer beads is 4 mm, these corresponding precisely to the dimensions indicated hereinabove for polymer beads before the fragrance has been adsorbed.

According to another specific feature, the first and second grilles 3, 4 are planar and mutually parallel, when fixed into the frame 2. In addition, the bars 31, 32, 33, . . . , 41, 42, 43, . . . of each grille are straight and mutually parallel. Furthermore, each bar 31, 32, 33, . . . of the first grille 3 faces a bar 41, 42, 43, . . . of the second grille 4, as depicted in FIG. 1 where a bar 31 of the grille 3 hides a bar 41 of the grille 4.

The capsule is thus advantageously easy to manufacture on an industrial scale, as the shapes of the grilles and of their bars are as simple as possible. Furthermore, the air flow passing through the capsule is advantageously close to a laminar air flow. This is because since a bar of the first grille 3 faces a bar of the second grille 4, the bars form less of an obstacle to the air flow passing through the capsule. Because this air flow is thus disturbed as little as possible by the bars it is advantageously not significantly turbulent, notably downstream of the capsule.

According to another particular feature and as illustrated in FIG. 1, for each grille 3, 4, the distance 51 between two adjacent first bars 31, 32, 33, . . . , 41, 42, 43, . . . and the thickness 52 of each bar 31, 32, 33, . . . , 41, 42, 43, . . . are strictly smaller than the smallest initial and/or final dimension of the substrate elements 1. Further, as illustrated in FIG. 3, the spacing 53 between the first and second grilles 3, 4 is greater than the smallest initial dimension of the substrate elements 1 and smaller than the largest initial dimension of the substrate elements 1.

Typically, the thickness 52 of each bar is 0.8 mm.

Advantageously, the substrate elements 1 are thus at least initially kept clamped, or at least wedged, between the bars of the grilles 3, 4. Further, as their dimensions diminish, the substrate elements 1 become at least partially free to move around between the grilles 3, 4, without in any way being able to pass between the bars 31, 32, 33, . . . , 41, 42, 43, . . . .

According to another particular feature, at least two adjacent second bars 31, 32, 33, . . . , 41, 42, 43, . . . of the first grille 3 and/or the second grille 4 extend in the thickness of the frame 2. For example, these two adjacent second bars are the bars 45 and 47 illustrated in FIG. 3. Between these two adjacent second bars, a single row of substrate elements 1 of the layer of substrate elements can be held. In a first example corresponding to that depicted in FIG. 3, the two adjacent second bars 45 and 47 of the grille 4 extend in the thickness of the frame 2 until they touch the bars 35 and 37 of the other grille 3 (which are depicted in FIG. 2) that face them. In another example that has not been illustrated, said adjacent second bars of each grille 3 and 4 extend in the thickness of the frame 2 until they touch in the middle of the thickness of the frame 2.

It should be understood that the only requirement is to hold the substrate elements 1 initially placed in the row throughout the working life of the capsule, i.e. until the substrate elements have reached their final dimensions. Thus, in the first example hereinabove, it is permissible for there to be a spacing between each bar extending in the thickness of the frame 2 and the bar of the other grille 4 that faces it if this spacing is smaller than the smallest final dimension of the substrate elements.

Advantageously, the layer of substrate elements thus comprises at least one row of substrate elements. This row preferably contains a controlled number of substrate elements. When the substrate elements 1 are being loaded into the capsule 0 on an industrial scale, control over the number of substrate elements is easier if it concerns only those of the row, rather than all those of the layer.

Furthermore, the adjacent second bars 31, 32, 33, . . . , 41, 42, 43, . . . extending in the thickness of the frame 2 may be arranged vertically, as illustrated in FIG. 3. In this way, the substrate elements 1 of the row, of which there are seven in the illustration of FIG. 1, and which over time become to varying extents free to move around vertically between said adjacent second bars, compact down at least under the action of their weight. The height of the row therefore forms a visual indication of how used up the capsule 0 is. By way of example, a segment made up of ten spherical substrate elements 1 with a diameter of 3 mm has a length of 30 mm. If the diameter of each substrate element decreases by 20% on average under the effect of being used up, combined with gravity, the length of the segment becomes equal to 24 mm at least under the effect of gravity. One of the two bars that extend in the thickness of the frame may bear a marking indicating the height of the row at which the capsule, because it is empty, needs to be thrown away and replaced with another.

Thus, the extent to which the capsule is used up can be observed simply and easily. In addition, the visual indication of how used up it is absolutely reliable because it depends on observing not a single substrate element but a plurality of substrate elements (those that make up the row). In that sense, the row constitutes an indicator of how used up it is on average, but is relatively independent of how used up a single substrate element considered in isolation might be, such substrate element usage potentially varying somewhat.

It is envisioned that a weight will be placed on top of the row of beads in order to ensure that the row compacts down.

Also, for this purpose, it is envisioned that this weight will be made of a magnetic material and that the capsule will further comprise a permanent magnet arranged for example in the frame 2. More specifically and by way of example, the magnet is able to attract said weight and is arranged underneath the row. In another example, the magnet is able to repel said weight and is arranged at the top of the row.

It is also envisioned that the row compaction function will be performed not using a weight, magnetic or otherwise, but using a spring. This spring would be fixed by a first end into the frame 2 of the capsule 0 in the region of the row, and an end stop would be fixed to the other end of the spring so that, regardless of how used up the substrate elements of which the row is composed are, the spring is kept in a state of compression between the frame 2 and the end stop and so that the row is correspondingly compacted down between the end stop and the frame 2. It will be appreciated that this arrangement advantageously performs the function of compacting the row of substrate elements 1, whether this row is arranged vertically or horizontally.

Furthermore, it is envisioned for the power of the air flow generator (insofar as this power is variable) to be slaved to the height of the row, so as to maintain a fragrance molecule flow rate that is constant despite the beads progressively being used up. For example, between the initial height of the row and a smaller final height, the power of the air flow generator is advantageously progressively increased. However, it should be noted that the quantity of fragrance molecules plucked for a constant air flow is more or less unchanging with respect to the extent to which the substrate elements are used up, provided these still contain fragrance molecules, because this quantity is more greatly dependent on the surface area of the substrate elements swept by the air flow, which is substantially unchanging with respect to the extent to which the substrate elements are used up.

Moreover, the frame 2 may comprise at least one male attachment element 5 on one face and at least as many female attachment elements 6 on the other face, each male element being able to engage, preferably removably, with any one of the female elements. In this way, several capsules 0 can be joined together, their frames being juxtaposed in the direction of their thickness.

Figure 4:
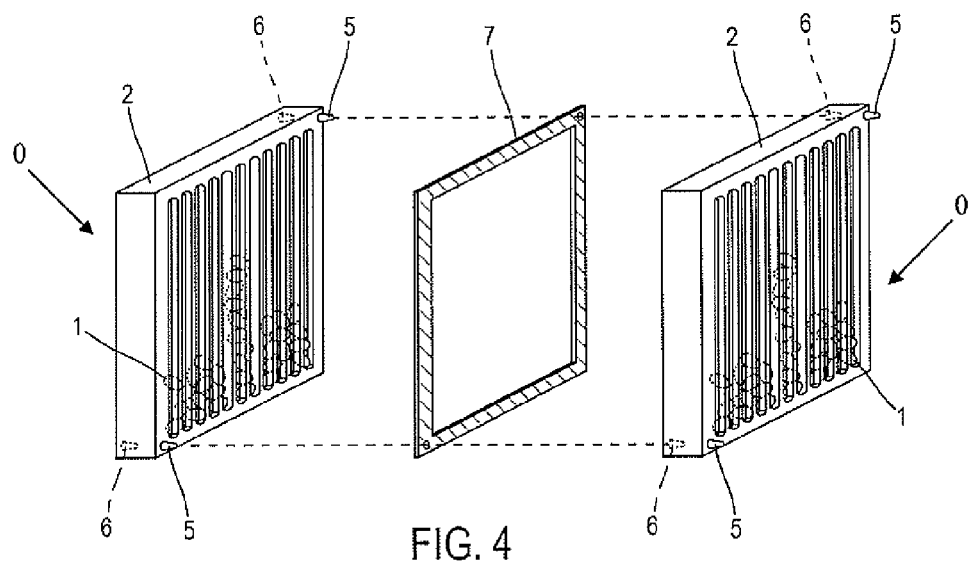
FIG. 4 illustrates how the capsules can be juxtaposed, and FIG. 5 schematically depicts a fragrance-diffusing device according to the invention.

For example, and as illustrated notably in FIGS. 2 and 4, two male attachment elements comprising frustoconically shaped fingers are arranged at two opposite corners of one of the faces of the frame, the other face of the frame having two female attachment elements comprising orifices made at two opposite corners of said other face. As illustrated in FIG. 4, this configuration allows the capsules to be juxtaposed with one another and mechanically held there, the fingers and the orifices being able to collaborate only if the capsules are precisely opposite one another and oriented in one and the same direction with each finger becoming wedged in each corresponding orifice, respectively.

Thus, juxtaposed capsules can be positioned and mechanically held together. Further, the quantity of fragrance molecules diffused is modifiable, notably according to the volume of the room that is to be scented. For example, if a capsule comprises a number of substrate elements such that it is able satisfactorily to scent a room of 30 cubic meters, then all that is required in order satisfactorily to scent a room of 60 cubic meters is to juxtapose two capsules of this type, because then twice as many fragrance molecules are diffused into the atmosphere. Furthermore, even though the same fragrance is adsorbed into the substrate elements of each capsule, it is advantageously possible to diffuse a mixture of fragrances by juxtaposing at least two capsules in which each has a different fragrance adsorbed into its substrate elements.

This possibility of juxtaposing capsules with one another is still compatible with a compact fragrance-diffusing device, namely one of small dimensions, because of the small thickness of the capsule 0.

Furthermore, and as illustrated in FIG. 4, an airtight seal 7 may be fitted at the junction between two juxtaposed frames 2.

The air flow passing through the capsules 0 juxtaposed by their frames 2 is thus forced to pass through each capsule 0 of the juxtaposition with no air flow pressure drop caused by air leaking between the frames 2 of the juxtaposed capsules 0.

It should be noted that the seal 7 may advantageously act as a male fixing element 5. For example, the seal 7 is partially inserted into a first groove made in the periphery of one face of the frame 2, another part of the seal 7 projecting from the face of the frame 2, and the other face of the capsule comprises a second groove equivalent to the first but containing no seal 7. In this example, a first capsule can be juxtaposed with another by inserting the protruding part of the seal 7 into the groove made in the periphery of the face of the frame 2 of the other capsule.

In the claims, the word "comprising" does not exclude other elements, and the indefinite article "a/an/one" does not exclude a plurality.

It should be obvious to persons skilled in the art that the present invention allows embodiments in numerous other specific forms without departing from the field of application of the invention as claimed. Therefore, the present embodiments are to be considered to be by way of illustration, and can be modified in the field defined by the scope of the attached claims.

The invention claimed is:

1. A fragrance capsule comprising:
   substrate elements into which a fragrance is adsorbed,
   a frame,
   a first grille and a second grille which are fixed in the frame facing one another, each grille comprising a plurality of bars,
   wherein the bars of one and the same grille being spaced apart and the grilles being spaced apart, so that the capsule allows a single layer of substrate elements to be held in the frame and between the grilles and allows air to circulate through the frame around the substrate elements and the bars.

2. The fragrance capsule as claimed in claim 1, wherein each substrate element has dimensions which vary over time from initial dimensions to smaller final dimensions reached when the fragrance has been fully desorbed.

3. The fragrance capsule as claimed in claim 2, wherein, for each grille, the distance between two adjacent first bars and the thickness of each bar are smaller than the smallest dimension of the substrate elements, and in that the spacing between the first and second grilles is greater than the smallest initial dimension of the substrate elements and smaller than the largest initial dimension of the substrate elements.

4. The fragrance capsule as claimed in claim 1, wherein:
   the first and second grilles are planar and mutually parallel, and
   the bars of each grille are straight and mutually parallel,
   so that each bar of the first grille faces a bar of the second grille.

5. The fragrance capsule as claimed in claim 1, wherein at least two adjacent second bars of the first grille and/or the second grille extend in the thickness of the frame so that a single row of substrate elements of the layer of substrate elements is held between the two adjacent second bars extending in the thickness of the frame.

6. The fragrance capsule as claimed in claim 5, wherein the adjacent second bars extending in the thickness of the frame are arranged vertically so that as the substrate elements of the row compact down over time at least under the action of their weight, the height of the row constitutes a visual indication of how used up the capsule is.

7. The fragrance capsule as claimed in claim 6, wherein a weight is arranged on top of the row of beads.

8. The fragrance capsule as claimed in claim 5, wherein a weight is arranged on top of the row of beads.

9. The fragrance capsule as claimed in claim 5, wherein it further comprises a spring attached by a first end to the frame in the region of the row and an end stop attached to the other end of the spring, so that the spring is kept compressed between the frame and the end stop irrespective of how used up the substrate elements are.

10. The fragrance capsule as claimed in claim 1, wherein the frame comprises at least one male attachment element on one face and at least as many female attachment elements on the other face, each male element being able to engage with any one of the female elements so that several capsules can be joined together with their frames juxtaposed in the direction of their thickness.

11. The fragrance capsule as claimed in claim 10, wherein an airtight seal is fitted at the junction between two juxtaposed frames.

12. A fragrance-diffusing device comprising:
    a capsule as claimed in claim 1,
    a ventilation passage,
    an air flow generator designed to propel air along the ventilation passage, and
    an attachment support designed for attaching the fragrance capsule in the ventilation passage,
    so that the propelled air diffuses the fragrance.

* * * * *